United States Patent [19]
Dietl

[11] Patent Number: 6,136,357
[45] Date of Patent: Oct. 24, 2000

[54] PHARMACEUTICAL PREPARATION CONTAINING CYCLOSPORIN(S) FOR ORAL ADMINISTRATION AND PROCESS FOR PRODUCING THE SAID PREPARATION

[75] Inventor: Hans Dietl, Bad Aibling, Germany

[73] Assignee: CicloMulsion AG, Karlsruhe, Germany

[21] Appl. No.: 09/051,173

[22] PCT Filed: Jul. 9, 1996

[86] PCT No.: PCT/EP96/03001
§ 371 Date: Sep. 14, 1998
§ 102(e) Date: Sep. 14, 1998

[87] PCT Pub. No.: WO97/12626
PCT Pub. Date: Apr. 10, 1997

[30] Foreign Application Priority Data

Oct. 4, 1995 [DE] Germany .......................... 195 37 012

[51] Int. Cl.$^7$ .................................................. A61K 38/00
[52] U.S. Cl. ................................ 426/435; 514/9; 514/11; 514/78; 514/885
[58] Field of Search .................................... 424/450, 435; 514/9, 11, 78, 885

[56] References Cited

U.S. PATENT DOCUMENTS

| | | | |
|---|---|---|---|
| 5,350,741 | 9/1994 | Takade | 514/3 |
| 5,527,537 | 6/1996 | Dietl | 424/450 |
| 5,529,785 | 6/1996 | Dietl | 424/450 |
| 5,622,714 | 4/1997 | Dietl | 424/450 |
| 5,637,317 | 6/1997 | Dietl | 426/450 |
| 5,639,474 | 6/1997 | Woo | 424/452 |
| 5,660,858 | 8/1997 | Parikh | 426/450 |

FOREIGN PATENT DOCUMENTS

| | | |
|---|---|---|
| 0 651 995 A1 | 5/1995 | European Pat. Off. . |
| 004315921 | 11/1993 | Germany . |

OTHER PUBLICATIONS

Database WPI, Section Ch, Week 9243, Derwent Publications Ltd., London, GB; & JP 04 253 907 A (Green Cross Corp.), Sep. 9, 1992, Abstract.

*Primary Examiner*—Gollamudi S. Kishore
*Attorney, Agent, or Firm*—Townsend and Townsend and Crew LLP

[57] ABSTRACT

Cyclosporin(s) are formulated as a pharmaceutical preparation that provides good and uniform resorption of the cyclosporin(s) with no nonphysiological pharmaceutical adjuvants, by combining the cyclosporin(s) with (i) monoglycerides, diglycerides, and/or triglycerides of natural fatty acids, (ii) natural fatty acids and/or alkaline salts of natural fatty acids, and (iii) 3-sn-phosphatidyl choline(s), and/or phosphatidyl ethanolamine(s), and optionally also (iv) natural bile acids and/or alkaline salts of natural bile acids, and (v) a natural alcohol. The pharmaceutical preparation does not contain water and is not an emulsion.

16 Claims, No Drawings

PHARMACEUTICAL PREPARATION CONTAINING CYCLOSPORIN(S) FOR ORAL ADMINISTRATION AND PROCESS FOR PRODUCING THE SAID PREPARATION

This application is a 371 of PCT/E896/03001, filed Jul. 9, 1996

BACKGROUND OF THE INVENTION

1. Field of the Invention

This invention relates to a novel pharmaceutical preparation for oral administration containing cyclosporin(s), a process for producing said pharmaceutical preparation and the use thereof for oral administration.

2. Description of the Prior Art

Cyclosporins are cyclic oligopeptides of lower fungi which have been discovered by scientists at Sandoz AG, Basel. Especially cyclosporin A and cyclosporin G, respectively, have been used as immunosuppressive agents, especially in graft transplants. Also preferred is the cyclosporin derivative "SDZ IMM 125", a hydroxyethyl derivative of D-serine-8-cyclosporin. The use in the case of other diseases, e.g. diabetes and psoriasis as well as numerous autoimmune disorders (e.g. rheumatoid arthritis, endogenous uveitis etc.) has also been described.

Cyclosporin A is obtained as a white amorphous powder from fungi by column chromatography over silica gel, it crystallizes from acetone in the form of white needles having a melting point of from 148 to 151° C. In addition to cyclosporin A, numerous other cyclosporins are known, ranging from cyclosporin A to cyclosporin Z (cf. Römpp's Chemie Lexikon, 9 th edition, pages 841–843). Semisynthetic derivatives of the cyclosporin are known as well and may be employed according to the present invention. Said derivatives are substances being chemically very similar to each other, and consisting of cyclic polypeptides of 11 amino acids, which are partly methylated. Cyclosporins are soluble in alcohol, ether, acetone, chlorinated hydrocarbons and natural oils (triglycerides of fatty acids).

Cyclosporin A is commercially available for oral application in the form of capsules as well as a solution for oral administration. In both presentation forms, the cyclosporin is dissolved in a mixture of ethanol with a vegetable oil (Pharmacopoeia Martindale, 29th edition, U.S. Pharm. XXII, 619, as well as the technical information Sandimmun® of Sandoz Company).

In addition to ethanol and vegetable oil (preferably corn oil) further adjuvants are used for the dissolution of cyclosporin A and to maintain it in dissolved form, e.g. poly(oxyethylene)-6-glycerol-tri(oleate, linoleate). The use of said adjuvants reveals the great problems involved in the oral administration of cyclosporin in a form which ensures at least partial resorption thereof.

The poly(oxyethylene)-6-glycerol-tri-oleates or linoleates used to achieve an improved solubility of the cyclosporins may have undesirable effects, they affect the resorption not only of the cyclosporins, but also of other substances, such as fats, paraffins, vitamins etc. Furthermore, the quantities employed of said adjuvants should not exceed 25 mg per kg body weight. Moreover, these substances may induce undesirable allergic reactions, which may be as intense as shock conditions. The major problem of the application forms of cyclosporin(s) described above for oral administration is that cyclosporin is resorbed poorly and that also this resorption varies widely. Resorption is incomplete and varies highly from patient to patient, even on a daily basis in the same patient. In general, resorption varies between 20 and 50% of the administered dose of cyclosporin(s). However, a uniform and homogenous resorption is extremely desirable. Moreover, it would be practical to have cyclosporin preparations which ensure a better overall resorption, i.e. an increased bioavailability.

Therefore, administration forms have been developed, in which cyclosporin was dissolved in a mixture, containing monoglycerides, diglycerides, triglycerides of fatty acids, alcohol, propylene glycol and macrogol glycerol hydroxystearate. This enables a better and more uniform resorption, but there are patients who show a hypersensitivity against the synthetic adjuvants propylene glycol and macrogol glycerol hydroxystearate.

Therefore, emulsions containing cyclosporin for oral administration have been developed which contain only natural adjuvants, i.e. in addition to water, natural fats, lecithins and alkaline salts of free fatty acids (German disclosure P4338086.7).

Said emulsions ensure an improved and a more uniform resorption of cyclosporin(s), and contain only pharmaceutical adjuvants of natural materials, such as natural fats, lecithins and alkaline salts of edible fatty acids. However, said emulsions suffer from the disadvantage that they essentially can only be administered in the form of a drinking solution. Its administration in capsules, in particular soft gelatin capsules, is not possible or only with significant effort, since the oil in water emulsion may attack the capsule shell.

SUMMARY OF THE INVENTION

Therefore, one object of the present invention is to provide a pharmaceutical presentation form containing cyclosporin(s), which permits a good and uniform resorption of the cyclosporin(s), and does not contain any nonphysiological pharmaceutical adjuvants, and which may administered in the form of a drinking solution as well as in the form of capsules.

The presentation form of the invention contains:

(A) cyclosporin(s)

(B) monoglycerides and/or diglycerides and/or triglycerides of natural fatty acids (=edible fatty acids)

(C) natural fatty acids (=edible fatty acids) and/or alkaline salts of natural fatty acids (D) 3-sn-phosphatidyl cholines and/or phosphatidyl ethanolamines

DESCRIPTION OF THE PREFERRED EMBODIMENTS

Additionally, the presentation form according to the present invention may also comprise natural bile acids and/or the salts thereof, e.g. glycocholic acid, tauroglycocholic acid and/or sodium glycolate, tauroglycocholic acid sodium salt.

In order to increase the solubility of cyclosporin(s) in the mixture of the present invention, said mixture may additionally contain monovalent and/or polyvalent alcohols, e.g. ethanol and/or glycerol. The mixture according to the present invention may be administered as such or following dilution with a liquid such as water, and also, however, in a capsule, in particular in the form of a soft gelatin capsule. In order to prevent the attack of gastric acid, the mixture according to the present invention may be applied in the form of an enteric coated capsule, which, however, is soluble in the small intestine, in particular in a soft gelatin capsule.

As cyclosporins, natural and synthetic cyclosporins, e.g. the well known cyclosporins A–Z may be used; cyclosporin A and cyclosporin G as well as the cyclosporin derivative SDZ IMM 125 are preferred.

As monoglycerides, diglycerides and triglycerides of natural fatty acids (=edible fatty acids) glycerides of natural fats, such as soybean oil, safflower oil, coconut oil (MCT oils), fish oils, corn oil, olive oil, sunflower oil may be used.

Monoglycerides, diglycerides and triglycerides in pure form as well as in the form of a mixture, e.g. a pure corn oil (=triglyceride) as well as a mixture, consisting of monoglycerides, diglycerides and triglycerides of corn oil may also be employed.

Preferably used are mixtures, containing monoglycerides, diglycerides and triglycerides of natural fatty acids. Particularly preferred are mixtures of natural fatty acids (=edible fatty acids), containing 20–60% triglycerides,
15–50% diglycerides and
3–20% monoglycerides.

As free fatty acids or alkaline salts of free fatty acids (=edible fatty acids), respectively, may be used for example myristic acid and/or palmic acid and/or stearic acid and/or oleic acid and/or linoleic acid and/or linolenic acid etc., their sodium and/or potassium salts or mixtures thereof. The amounts employed are approximately 0.2–25%, based on the total amount of monoglycerides, diglycerides and triglycerides, 0.5–10% being preferred. The salts are preferred over the free fatty acids.

3-sn-Phosphatidyl cholines and/or phosphatidyl ethanolamines may be used in pure form or as a mixture. Preferred are the lecithins, containing both phosphatidyl cholines and phosphatidyl ethanolamines, e.g. lecithins from soybean and/or egg. Most suitable are lecithins having a content of more than 50% 3-sn-phosphatidyl choline and/or partially hydrogenated phosphatidyl choline and/or hydrogenated phosphatidyl choline. Generally and preferably, the amount of the lecithins is 3–25 wt. %, based on the total weight of the mixture according to the present invention.

Natural bile acids and/or the salts thereof further improve the resorption of cyclosporin(s) from the mixture according to the invention. This effect is particularly distinct, if on account of a specific disease the patient concerned does not produce any or not enough endogenic bile acids.

Additionally, in order to achieve the desired increased solubility of the cyclosporin(s), natural alcohols may be used, in particular ethyl alcohol and/or glycerol in concentrations up to approximately 30 wt. % of the total mixture.

Immediately after the mixture of the present invention is mixed with water and slightly agitated or stirred, e.g. by using a spoon in a glass, an emulsion having an opaque appearance is formed, the droplets of which are about 5 $\mu$m up to about 100 $\mu$m in diameter. A similar emulsion is formed, when the mixture is administered in a soft gelatin capsule and the mixture of the invention is contacted with water in the gastro-enteric tract. In order to avoid the acidic milieu of the stomach, it may be favorable to administer the mixture of the present invention in an enteric coated capsule being soluble in the small intestine, preferably a soft gelatin capsule. By this, the mixture of the present invention is directly released at the site of resorption, i.e. the small intestine.

By the formation of a microemulsion, there is achieved an improved and more uniform resorption of the cyclosporin. As a result, the resorption is not only increased, but above all more uniform and to a great extent independent of the variations caused by the simultaneous intake of different nutrients. This enables both a more reasonable therapy as well as a closer control of the blood levels of cyclosporin.

The following working examples illustrate the preparation of the present invention as well as the method for the production thereof. However, the invention is not limited thereto.

EXAMPLE 1

50 g of cyclosporin A are dissolved in 810 g of a mixture of monoglycerides, diglycerides and triglycerides, obtained from corn oil, under stirring at 70° C. Then, 15 g of sodium oleate and 125 g of soybean lecithin are added and the stirring is continued.

a) The preparation thus obtained is poured into 100 ml flasks under addition of a preservative such as sodium benzoate. Addition of 1 ml of this to 1 ml of water followed by slightly stirring or agitating results in an opaque emulsion.

b) The preparation is filled into enteric coated capsules being soluble in the small intestine in quantities of 1 g each in a manner known per se.

EXAMPLE 2

The production of the pharmaceutical preparation of the invention is performed as described in example 1, except that 50 g of cyclosporin, 750 g of a mixture of mono, di and triglycerides, obtained from corn oil, 125 g of egg lecithin, 10 g of sodium oleate and 65 g of the sodium salt of tauroglycocholic acid are used.

EXAMPLE 3

75 g of cyclosporin A are dissolved in 120 g ethyl alcohol and 700 g soybean oil under stirring (at approx. 60–70° C.). Then, 40 g of potassium oleate, 50 g of soybean lecithin and 15 g of sodium glycocholic acid are added and stirring is continued. On mixing with 500 g of water, the pharmaceutical preparation obtained forms a microemulsion, having droplets of a size between 10 and 100 $\mu$m.

What is claimed is:

1. A pharmaceutical preparation containing cyclosporin(s) for oral administration, comprising the following components:

(A) a cyclosporin, (B) a member selected from the group consisting of monoglycerides, diglycerides, and triglycerides of natural fatty acids, and combinations thereof, (C) a member selected from the group consisting of natural fatty acids, alkaline salts of natural fatty acids, and combinations thereof, and (D) a substance containing a member selected from the group consisting of
3-sn-phosphatidyl choline(s), phosphatidyl ethanolamine(s), and combinations thereof;

with the proviso that said pharmaceutical preparation does not contain water and is not an emulsion.

2. A pharmaceutical preparation in accordance with claim 1, further comprising as an additional component a member selected from the group consisting of natural bile acids, alkaline salts of natural bile acids, and combinations thereof.

3. A pharmaceutical preparation in accordance with claim 1, further comprising as an additional component a natural alcohol.

4. A pharmaceutical preparation in accordance with claim 1 in which component (B) is a mixture of monoglycerides, diglycerides, and triglycerides of natural fatty acids, in which said triglycerides constitute 20–60% by weight of said preparation, said diglycerides constitute 15–50% by weight of said preparation, and said monoglycerides constitute 3–20% by weight of said preparation.

5. A pharmaceutical preparation in accordance with claim 1, in which component (D) is a lecithin of natural origin.

6. A pharmaceutical preparation in accordance with claim 5 in which said lecithin is a member selected from the group consisting of soybean lecithin, egg lecithin, and combinations thereof.

7. A pharmaceutical preparation in accordance with claim 1 in which said components are contained in an enteric coated capsule soluble in the small intestine.

8. A pharmaceutical preparation in accordance with claim 7 in which said enteric coated capsule is a gelatin capsule.

9. A process for the preparation of a pharmaceutical preparation comprising the following components:

(A) a cyclosporin, (B) a member selected from the group consisting of monoglycerides, diglycerides, and triglycerides of natural fatty acids, and combinations thereof, (C) a member selected from the group consisting of natural fatty acids, alkaline salts of natural fatty acids, and combinations thereof, and (D) a substance containing a member selected from the group consisting of
3-sn-phosphatidyl choline(s), phosphatidyl ethanolamine(s), and combinations thereof, said process comprising mixing said cyclosporin with components (B), (C), and (D) in a natural alcohol in the absence of water and without forming an emulsion.

10. A process for the preparation of a pharmaceutical preparation comprising the following components:

(A) a cyclosporin, (B) a member selected from the group consisting of monoglycerides, diglycerides, and triglycerides of natural fatty acids, and combinations thereof, (C) a member selected from the group consisting of natural fatty acids, alkaline salts of natural fatty acids, and combinations thereof, and (D) a substance containing a member selected from the group consisting of
3-sn-phosphatidyl choline(s), phosphatidyl ethanolamine(s), and combinations thereof, said process comprising dissolving said cyclosporin in a natural alcohol prior to combining said cyclosporin with components (B), (C), and (D), and doing so in the absence of water and without forming an emulsion.

11. A method for treating a subject by administration of cyclosporin(s), said method comprising orally administering to said subject a pharmaceutical preparation that does not contain water and is not an emulsion, said pharmaceutical preparation comprising the following components:

(A) a cyclosporin, (B) a member selected from the group consisting of monoglycerides, diglycerides, and triglycerides of natural fatty acids, and combinations thereof, (C) a member selected from the group consisting of natural fatty acids, alkaline salts of natural fatty acids, and combinations thereof, and (D) a substance containing a member selected from the group consisting of
3-sn-phosphatidyl choline(s), phosphatidyl ethanolamine(s), and combinations thereof.

12. A process in accordance with claim 9 further comprising mixing said cyclosporin and said components (B), (C), and (D) with a member selected from the group consisting of natural bile acids, alkaline salts of natural bile acids, and combinations thereof, in said natural alcohol.

13. A process in accordance with claim 10 further comprising combining said cyclosporin thus dissolved and said components (B), (C), and (D) with a member selected from the group consisting of natural bile acids, alkaline salts of natural bile acids, and combinations thereof.

14. A process in accordance with claim 11 in which said pharmaceutical preparation further comprises a member selected from the group consisting of natural bile acids, alkaline salts of natural bile acids, and combinations thereof.

15. A process in accordance with claim 11 in which said pharmaceutical preparation further comprises a natural alcohol.

16. A process in accordance with claim 11 in which said pharmaceutical preparation further comprises:

(E) a member selected from the group consisting of natural bile acids, alkaline salts of natural bile acids, and combinations thereof, and (F) a natural alcohol.

* * * * *